United States Patent [19]

Paul et al.

[11] Patent Number: 5,667,966
[45] Date of Patent: Sep. 16, 1997

[54] MOUSE MONOCLONAL ANTIBODIES TO HEPATITIS E VIRUS AND METHODS FOR USING SAME

[75] Inventors: Deborah A. Paul, Gurnee; Mark F. Knigge, Grayslake, both of Ill.

[73] Assignee: Abbott Laboratories, Abbott Park, Ill.

[21] Appl. No.: 701,554

[22] Filed: Aug. 22, 1996

Related U.S. Application Data

[63] Continuation of Ser. No. 492,606, Jun. 20, 1995, abandoned, which is a continuation of Ser. No. 172,700, Dec. 22, 1993, abandoned.

[51] Int. Cl.$^6$ .......................... C12Q 1/70; G01N 33/576; C07K 16/08; C12N 5/18
[52] U.S. Cl. .......................... 435/5; 435/339; 530/388.3; 436/820
[58] Field of Search .................................. 435/5, 240.27; 436/518, 548, 820; 530/388.3

[56] References Cited

FOREIGN PATENT DOCUMENTS

| 0335135 | 10/1989 | European Pat. Off. . |
| 9314116 | 7/1993 | WIPO . |
| 9314208 | 7/1993 | WIPO . |

OTHER PUBLICATIONS

Antibodies, A Laboratory Manual, Ed Harlow, Cold Spring Harbor Laboratory and David Lane, Imperial Cancer Research Fund Laboratories. Cold Spring Harbor Laboratory 1988, pp. 567–569.

"Epitope Mapping in Proteins of Hepatitis E Virus", Y. E. Khudyakov, et al., *Virology*, vol.: 194, No. 1, pp. 89–96 (May 1993).

"Hepatitis E Virus (HEV): Molecular Cloning and Sequencing of the Full–Length Viral Genome", A.W. Tam, et al., *Virology*, vol.: 185, No. 1, pp. 120–131, (1991) New York, NY, USA.

"Human Linear B–cell Epitopes Encoded by the Hepatitis E Virus Include Determinants in the RNA–Dependent RNA Polymerase", M. Kaur, et al., *Proceeding of the National Academy of Sciences of the USA*, vol.: 89, No. 9, 1 May 1992 Washington, D.C.

Sevier et al., Monoclonal Antibodies in Clinical Immunology, Clin. Chem. 27(11):1797–1806, 1981.

Kaur et al., Human linear B–cell epitopes encoded by the hepatitis E virus include determinants in the RNA–dependent RNA polymerase, Proc. Natl. Acad. Sci. 89:3855–3858, 1992.

Yarbough et al., Hepatitis E Virus Identification of Type–Common Epitopes, J. Virol. 65(11):5790–5797, 1991.

*Primary Examiner*—Marian C. Knode
*Assistant Examiner*—Donna C. Wortman
*Attorney, Agent, or Firm*—Priscilla E. Porembski

[57] ABSTRACT

Monoclonal antibodies are described which specifically bind to Hepatitis E Virus (HEV), and more particularly to HEV orf-3 antigen. Also provided are hybridoma cell lines which secrete these monoclonal antibodies, methods for using these monoclonal antibodies, and assay kits which contain these monoclonal antibodies.

7 Claims, 1 Drawing Sheet

MOUSE MONOCLONAL ANTIBODIES TO HEPATITIS E VIRUS AND METHODS FOR USING SAME

This application is a Continuation of application Ser. No. 08/492,606, filed Jun. 20, 1995 abandoned, which is a Continuation of application Ser. No. 08/172,700, filed Dec. 22, 1993 abandoned.

BACKGROUND OF THE INVENTION

This invention relates generally to antibodies which specifically bind to Hepatitis E Virus (HEV), and more particularly, relates to a novel hybridoma cell line which secretes monoclonal antibodies to HEV orf-3 antigen, and methods for using these monoclonal antibodies.

HEV, variously referred to as waterborne, epidemic or enterically transmitted non-A, non-B hepatitis (ET-NANBH), has a global distribution and has been noted as the cause of major endemic outbreaks of viral hepatitis in developing countries. D. W. Bradley et al., Br. Med. Bull. 46:442–461 (1990). Sporadic cases of ET-NANBH, as well as imported travel exposure, have been reported in developed countries. S. J. Skidmore et al., Lancet 337:1541 (1991). Although the fecal-oral route of transmission predominates, limited person-to-person routes of exposure have been suggested in some epidemiological studies. O. Velasquez et al., J. Amer. Med. Assoc. 363:3281–3285 (1990). This disease has been documented as having a high mortality rate of approximately 20% in pregnant women infected during their third trimester of pregnancy. See D. W. Bradley et al., supra.

Molecular cloning of the putative agent of HEV has been hampered by the lack of a tissue culture system for virus propagation. However, the use of available animal models and a newly developed non-specific amplification procedure have allowed the identification of a unique cDNA clone (identified as "ET 1.1") obtained from bile of cynomolgus macaques infected with a Burmese strain of HEV. A. G. Andjaparidze et al., Vopr. Virusol. 1:73–80 (1986), D. W. Bradley et al., Proc. Natl. Acad. Sci. USA 84:6277–6281 (1987) and G. W. Reyes et al., Science 247:1335–1339 (1990). Successful confirmation of the viral origin of this clone led to the identification of similar sequences in human fecal specimens collected from ET-NANBH epidemics in Somalia, Tashkent, Borneo, Pakistan and Mexico. G. R. Reyes et al., supra. cDNA libraries also have been prepared from human stool samples obtained during an ET-NANBH outbreak in Mexico. G. R. Reyes et al., Gastroenterol. Japon. 26:142–147 (1991). Immunoscreening of these cDNA libraries led to the identification of two cDNA clones which encode epitopes specific for HEV. P. O. Yarbough et al., J. Virol. 65:5790–5797 (1991). The isolation and sequencing of a set of overlapping cDNA clones led to the recognition that this form of hepatitis is caused by a novel virus unlike any of the other molecularly characterized agents of viral hepatitis. A. W. Tam et al., Virology 185:12–131 (1991).

Various regions of the HEV genome have been cloned and expressed in E. coli as fusion proteins with glutathione-S-transferase (GST). See, for example, S. J. Skidmore et al., supra. Four of these recombinant antigens, two derived from a Burmese (B) strain of HEV and two derived from a Mexican (M) strain of HEV, have been shown to contain antigenic sites recognized by antibodies from individuals previously exposed to HEV. See, P. O. Yarbough et al., supra. The two antigens from the Mexican strain, named M3-2 and M4-2, correspond to amino acid sequences at the carboxy-terminus of the second open reading frame (ORF-2) and the third open reading frame (orf-3), respectively. The two antigens from the Burmese strain, B 3-2 and B 4-2, correspond to amino acid sequences at the carboxy-terminus of orf-2 and orf-3, respectively. The M 3-2 and B 3-2 recombinant antigens both comprise 42 amino acids from the carboxy terminus of ORF-2. The degree of amino acid homology between these sequences of 42 amino acids is 90.5%. Id. The M 4-2 and B 4-2 recombinant antigens each comprise 33 amino acids from the carboxy terminus of orf-3; the degree of homology between these two sequences of 33 amino acids is 73.5%. Id.

Tests developed for detection of HEV must contain reagents which are useful for determining the specific presence of the virus in a test sample. The need therefore exists for reagents, such as monoclonal antibodies, capable of reacting only with HEV. Additionally, the ability to produce pure, specific monospecific antibodies is clearly of great importance for accurate identification, characterization, and purification of the HEV antigen.

While methods are available to confirm screening assay results for agents such as HIV, these techniques are not yet available for confirming the presence of HEV. Methods such as culturing HEV in vitro and a viral-based Western blot test are not available. While the detection of HEV nucleic acid may be done by performing PCR, this technique is tedious and expensive, requires special equipment such as a thermocycler, and turn-around time is up to 24 hours. Immunoelectron microscopy (IEM) has been used to confirm the presence of anti-HEV antibody, but the use of IEM is cost prohibitive as a routine confirmatory tool.

It therefore would be advantageous to provide a monoclonal antibody which can be used in accurate, rapid and cost effective methods for screening for HEV antigens or HEV antibodies in a test sample.

SUMMARY OF THE INVENTION

The present invention provides a highly specific and novel monoclonal antibody or fragment thereof that can be employed for the detection of HEV orf-3 antigen. The monoclonal antibody specifically binds to the HEV orf-3 protein at the carboxy terminal. The hybridoma which secretes the monoclonal antibody is identified as: Hybridoma cell line H67C46 (A.T.C.C. deposit No. HB 11522, secreting monoclonal antibody (H67C46). The specificity of this monoclonal antibody enables the advantageous identification of HEV-orf-3 antigen, which identification can be useful in viral differentiation studies as well as in the diagnosis and evaluation of HEV infections.

The monoclonal antibody of the present invention can be used in an immunoassay for the detection of HEV antigen or antibody. Many such immunoassay formats are known in the an and can be modified by adding a known amount of a monoclonal antibody which specifically binds to HEV orf-3 antigen.

A particularly preferred assay format is a competitive assay for determining the presence and amount of HEV antibody which may be present in a test sample. The assay involves contacting a test sample suspected of containing HEV antibodies with a solid phase coated with HEV antigens and an indicator reagent comprising a signal generating compound and a monoclonal antibody which specifically binds to HEV orf-3 antigen, for a time and under conditions sufficient to form antigen/antibody complexes of the test sample and solid phase and/or indicator reagent and solid phase; and determining the presence of HEV antibody present in the test sample by detecting the reduction in binding of the indicator reagent to the solid phase as compared to the signal generated from a negative test sample to indicate the presence of HEV antibody in the test sample Assay kits which contain the monoclonal antibody of the present invention are also described.

DETAILED DESCRIPTION OF THE INVENTION

Figure 1:
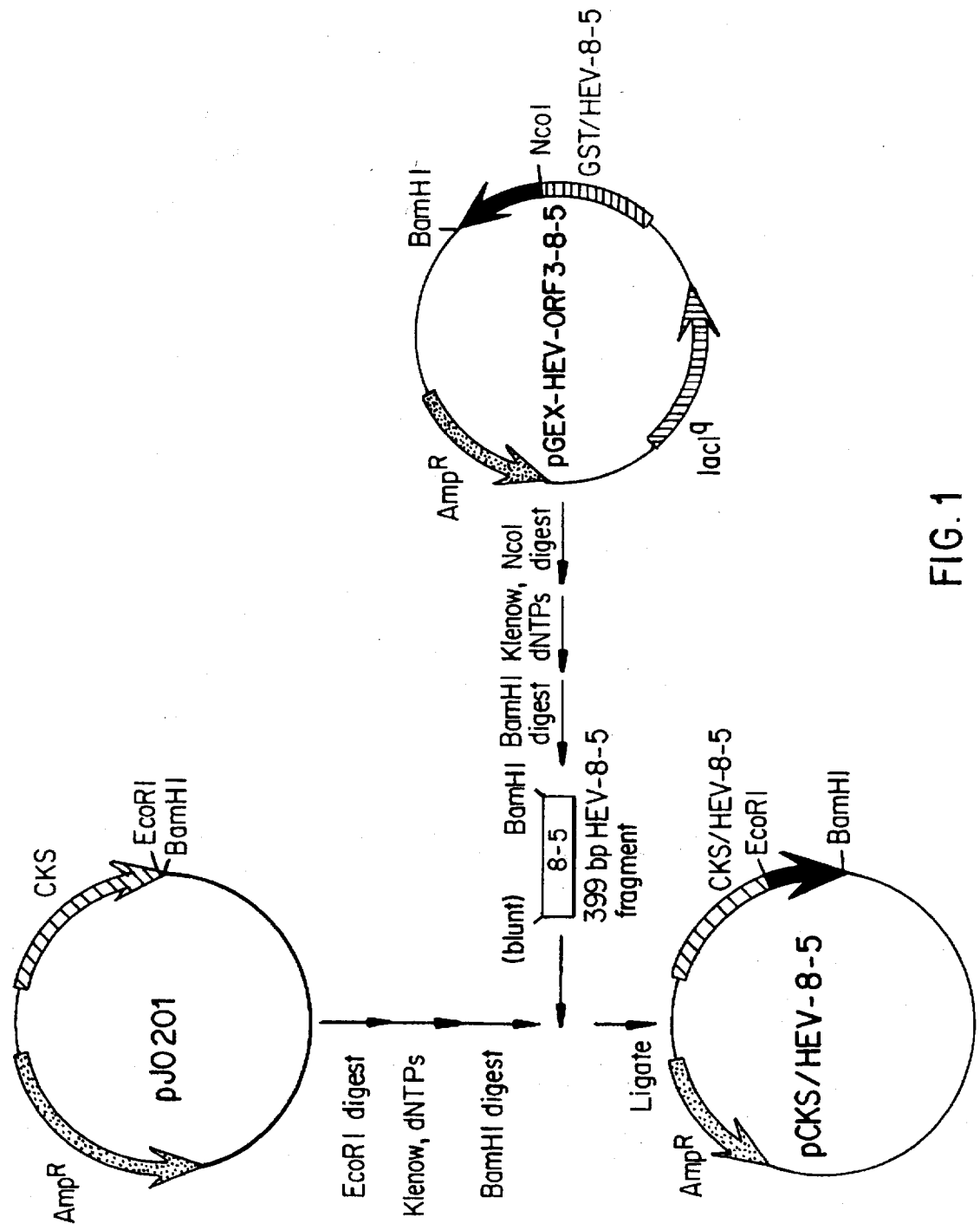
FIG. 1 is a schematic representation of the plasmid used for production of orf-3 CKS/HEV 8-5 antigen from plasmids pJO201 and pGEX-HEV-ORF3-8-5.

The monoclonal antibody of the present invention can be employed in various assay systems to determine the presence, if any, of HEV antigens or HEV antibodies in a test sample. Fragments of the monoclonal antibody provided also may be used.

The monoclonal antibody of the present invention may be screened for as follows. Recombinant or synthetic HEV orf-3 antigen is used on a solid phase (preferably, polystyrene beads). For example, the CMP-KDO synthetase (CKS) HEV recombinant orf-3 (8-5), obtained as described in Example 1, below is coated on the solid phase in the unpurified (extracted and solubilized) form. Alternately, an immunoassay (EIA) which uses the synthetic peptide spB4-2 (obtained as described in copending application U.S. Ser. No. 08/089,877 filed Jul. 9, 1993) on the solid phase is utilized. Detection of non-specific binding is accomplished by coating the solid phase with CKS alone or with a non-HEV CKS recombinant protein. Test samples (mouse serum, tissue culture supernatant, or mouse ascites fluid) are serially diluted in a specimen diluent and a portion is incubated with each solid phase for 1–2 hours at 40° C. Beads are then washed with buffer and bound antibody is detected using horseradish peroxidase (HRPO)-labeled second antibody. Beads are incubated with conjugate for a sufficient time at 40° C., and washed as before. An appropriate substrate solution is added in a dark at room temperature for 30 minutes. Sulfuric acid is added to stop the reaction, and the amount of color generated is determined by measuring the absorbance of the substrate at 492 nm within 2 hours of sulfuric acid addition. Details of this method are described in the example section, below.

For example, in a preferred assay format, the monoclonal antibody of the invention can be employed as a competitive probe for the detection of antibodies to HEV antigen. For example, HEV antigens coated on a solid phase, are contacted with a test sample suspected of containing antibody to HEV, and incubated with an indicator reagent comprising a signal generating compound which generates a measurable signal attached to the monoclonal antibody of the invention for a time and under conditions sufficient to form antigen/antibody complexes of the test sample to the solid phase or the indicator reagent to the solid phase. The reduction in binding of the monoclonal antibody of the invention to the solid phase, as evidenced by a reduction in the generated signal, can be quantitatively measured. A measurable reduction in the signal compared to the signal generated from a confirmed negative HEV test sample would indicate the presence of anti-HEV antibody in the test sample.

In an alterative assay method for detection of HEV antigens, a polyclonal or monoclonal anti-HEV antibody or a fragment thereof, which has been coated on a solid phase, is contacted with a test sample which may contain HEV antigens, to form a mixture. This mixture is incubated for a time and under conditions sufficient to form antigen/antibody complexes. Then, an indicator reagent comprising a monoclonal or a polyclonal antibody or a fragment thereof, which specifically binds to HEV antigen, to which a signal generating compound which generates a measurable signal has been attached, is contacted with the antigen/antibody complexes to form a second mixture. This second mixture then is incubated for a time and under conditions sufficient to form antibody/antigen/indicator reagent complexes. The presence of HEV antigen present in the test sample and captured on the solid phase, if any, is determined by detecting the measurable signal generated by the signal generating compound. The amount of HEV antigen present in the test sample is proportional to the signal generated.

Attentively, a polyclonal or monoclonal anti-HEV antibody or fragment thereof which is bound to a solid support, the test sample and an indicator reagent comprising a monoclonal or polyclonal antibody or fragments thereof, which specifically binds to HEV antigen to which a signal generating compound which generates a measurable signal is attached, are contacted simultaneously to form a mixture. This mixture is incubated for a time and under conditions sufficient to form antibody/antigen/indicator reagent complexes. The presence, if any, of HEV antigen present in the test sample and captured on the solid phase is determined by detecting the measurable signal generated by the signal generating compound. The amount of HEV antigen present in the test sample is proportional to the signal generated. In this or the assay format described above, the monoclonal antibody of the invention can be employed either as the capture phase or as pan of the indicator reagent.

In yet another detection method, the monoclonal antibody of the present invention can be employed in the detection of HEV antigen in fixed tissue sections, as well as fixed cells by immunohistochemical analysis, by standard methods well-known to those skilled in the art.

In addition, the monoclonal antibody can be bound to mantrices similar to CNBr-activated sepharose and used for the affinity purification of specific HEV antigens from cell cultures, or biological tissues such as blood and liver.

The monoclonal antibody of the invention also can be used for the generation of chimeric antibodies for therapeutic use, or other similar applications.

The monoclonal antibody or fragment thereof can be provided individually to detect HEV antigen. Combinations of the monoclonal antibody (and fragments thereof) of the present invention provided herein also may be used in combination with other monoclonal antibodies that have differing specificities for HEV as components in a mixture or "cocktail" of HEV antibodies, each having different binding specificities. Thus, this cocktail can include the monoclonal antibody of the invention directed to off-3 protein from the HEV genome, along with different monoclonal antibodies directed to other HEV regions, such as the off-2 protein or other binding sites on orf-3 HEV proteins. This cocktail of monoclonal antibodies would then be used in place of the single monoclonal antibody as described in the assay formats herein.

The polyclonal antibody or fragment thereof which can be used in the assay formats should specifically bind to HEV antigen. The polyclonal antibody used preferably is of mammalian origin and includes but is not limited to human, goat, rabbit or sheep anti-HEV polyclonal antibody. The polyclonal antibodies used in the assays can be used either alone or as a cocktail of polyclonal antibodies. Since the cocktails used in the assay formats are comprised of either monoclonal antibodies or polyclonal antibodies having different HEV specificity, they would be useful for diagnosis, evaluation and prognosis of HEV infection, as well as for studying HEV protein differentiation and specificity.

Test samples which can be tested by the methods of the present invention described herein include human and animal body fluids such as whole blood, serum, plasma, cerebrospinal fluid, urine, biological fluids such as cell culture supernatants, fixed tissue specimens and fixed cell specimens.

The "solid phase" is not critical and can be selected by one skilled in the art. Thus, latex particles, microparticles, magnetic or non-magnetic beads, membranes, plastic tubes, walls of microliter wells, glass or silicon chips and tanned sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microliter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable.

It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns.

To change or enhance the intrinsic charge of the solid phase, a charged substance can be coated directly to the material or onto microparticles which then are retained by a solid phase support material. Alternatively, microparticles can serve as the solid phase, by being retained in a column or being suspended in the mixture of soluble reagents and test sample, or the particles themselves can be retained and immobilized by a solid phase support material. By "retained and immobilized" is meant that the particles on or in the support material are not capable of substantial movement to positions elsewhere within the support material. The particles can be selected by one skilled in the art from any suitable type of particulate material and include those composed of polystyrene, polymethylacrylate, polypropylene, latex, polytetrafluoroethylene, polyacrylonitrile, polycarbonate, or similar materials. The size of the particles is not critical, although it is preferred that the average diameter of the particles be smaller than the average pore size of the support material being used. Thus, embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP Publication No. 0326100, and U.S. patent application Ser. No. 375,029 (EP Publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115.

Also, the methods of the present invention can be adapted for use in systems which utilize microparticle technology including automated and semi-automated systems wherein the solid phase comprises a microparticle. Such systems include those described in pending U.S. patent application Ser. No. 425,651 and U.S. Pat. No. 5,089,424, which correspond to published EPO applications Nos. EP O 425 633 and EP O 424 634, respectively, and U.S. Pat. No. 5,006,309.

The indicator reagent comprises a signal generating compound (label) which is capable of generating a measurable signal detectable by external means conjugated (attached) to a specific binding member for HEV. "Specific binding member" as used herein means a member of a specific binding pair. That is, two different molecules where one of the molecules through chemical or physical means specifically binds to the second molecule. In addition to being an antibody member of a specific binding pair for HEV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HEV as in a sandwich assay, to the capture reagent as in a competitive assay, or to the ancillary specific binding member as in an indirect assay.

The various signal generating compounds (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP publication 0326100, and U.S. patent application Ser. No. 375,029 (EP publication no. 0406473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115, which enjoys common ownership and which is incorporated herein by reference.

Also, the methods of the present invention can be adapted for use in systems which utilize microparticle technology including in automated and semi-automated systems wherein the solid phase comprises a microparticle. Such systems include those described in pending U.S. patent applications 425,651 and 425,643, which correspond to published EPO applications Nos. EP 0 425 633 and EP 0 424 634, respectively, which are incorporated herein by reference.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wisc.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio]propionate), SMCC (succinimidyl-4-[N-maleimidomethyl]cyclohexane-1-carboxylate), SIAB (succinimidyl [4-iodoacetyl] aminobenzoate), and SMPB (succinimidyl 4-[1-maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent applications Ser. No. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the monoclonal antibody of the present invention can be utilized in non-solid phase assay systems. These assay systems are known to those skilled in the art, and are considered to be within the scope of the present invention.

The monoclonal antibody of the invention can be used as a positive control in an assay which is designed to detect the presence of HEV antibody. In an assay which detected the presence of HEV antibody in a test sample, HEV antigens would be used as a capture phase. These HEV antigens could be prepared by various means from viral lysates, synthetic peptides of various immunogenic regions of the HEV genome, and/or recombinant proteins produced by using either synthetic or native antigens or epitopes of antigens. It also is contemplated that these types of HEV antigens could be employed in a variety of assay formats including those described herein as either the capture phase or detection phase. The use of the monoclonal antibody of the invention would ensure that the reagents provided to detect HEV antibody were performing adequately by being used in place of a test serum in the performance of the assay, according to procedures known to those of ordinary skill in the art.

It is contemplated that the reagent employed for the assay can be provided in the form of a kit with one or more containers such as vials or bottles, with each container containing a separate reagent such as a monoclonal antibody, or a cocktail of monoclonal antibodies, employed in the assay. These kits also could contain vials or containers of other reagents needed for performing the assay, such as washing, processing and indicator reagents.

The following examples demonstrate the advantages and utility of the H67C46 monoclonal antibody of the invention by describing methods for the development, characterization, epitope mapping and clinical utility of the monoclonal antibodies. The methods used for monoclonal antibody development follow procedures known in the art and detailed in Kohler and Milstein, *Nature* 256:494 (1975), and reviewed in J. G. R. Hurrel, ed., *Monoclonal Hybridoma Antibodies: Techniques and Applications*, CRC Press, Inc., Boco Raton, Fla. (1982).

To practice the invention, a recombinant DNA clone was constructed to contain the gene encoding the full length orf-3 of HEV as a fusion protein with CKS. The antigen (designated 8-5 protein) was used to immunize a mouse from which an immune splenocyte was fused to a SP2/0-Ag14 myeloma cell to produce a hybridoma cell line that secretes a monoclonal antibody of immunoglobulin (Ig) class $G_1$ (IgG$_1$) reactive with HEV orf-3. The resultant immunoglobulin was produced in mouse ascites fluid and was purified by affinity chromatography.

The examples set forth below are meant to illustrate, but not to limit, the spirit and scope of the invention.

EXAMPLE 1

Generation and Characterization of Hybridoma

A. Production of recombinant HEV Protein.

Plasmid pGEX-HEV-ORF3-8-5 (FIG. 1) was obtained from Genelabs, Inc., Redwood City, Calif. and encodes the complete 123 amino acids of orf-3 antigen of HEV as a glutathione S-transferase (GST) fusion in the pGEX expression system. The gene encoding the full length HEV orf-3, designated as the 8-5 protein, (see P. O. Yarbough, et al., supra) was cloned and expressed as a chimeric fusion protein with CMP-KDO synthetase (CKS) in plasmid pJ0201 in *E. coli* according to methods known in the art. The CKS/HEV-8-5 protein was expressed in *E. coli* strain XL1-Blue at greater than 20% of total cell protein after induction with isopropyl b-D thiogalactoside (IPTG). The clones were propagated in 10 liter fermentors, yielding 170–260 grams of wet cell paste per fermentation.

B. CKS-HEV Protein Solubilization.

The *E. coli* cells expressing the 8-5 protein were lysed at pH 10 in the presence of various protease inhibitors. The CKS fusion protein was insoluble and remained in the pellet after centrifugation. Pellets were washed with various detergents to remove non-specific proteins. Following solubilization in Tris, pH 8.5 containing 0.5% SDS, the CKS fusion protein was found to represent 50 to 60% of the total protein as evaluated by SDS-PAGE and gel densitometry. The solubilized protein was further purified by Sephacryl S-300HR column chromatography. Fractions were analyzed by SDS-PAGE, pooled and evaluated for purity by gel densitometry. Final purified protein was greater than 90% pure.

C. Immunization of Mice

The immunization regimen (4 mice) consisted of an initial immunization with additional immunizations at six and nine weeks. For the primary immunization, 10 µg CKS-HEV orf-3 8-5 extracted and solubilized (unpurified) recombinant protein, prepared as described above, was emulsified in complete Freund's adjuvant. Four mice (Balb/c) were inoculated intraperitoneally with this emulsion. At three weeks post-immunization, mouse serum was screened for enzyme immunoassay (EIA) immunoreactivity as described below. The serum anti-HEV titer tested against beadcoated with HEV 8-5 was $10^6$ in specimen diluent with no *E. coli* or CKS lysate added and $10^5$ in specimen diluent containing *E. coli* and CKS lysate, thus indicating only a 10-fold reactivity to non-specific proteins. The mouse serum antibody titer against beads coated with HEV orf-3 synthetic peptide spB4-2, prepared as described in copending U.S. patent application Ser. No. 07/089,877 filed Jul. 9, 1993 was $5 \times 10^3$, indicating reactivity to the carboxyl terminus of the HEV orf-3 protein.

Six weeks after the first immunization, two mice were boosted intraperitoneally with 10 µg of the immunizing protein in incomplete Freund's adjuvant. At week nine, post-immunization anti-HEV titers against beads coated with protein HEV 8-5 described above were $6.25 \times 10^6$ in specimen diluent with no additives to block out unwanted reactivity, $2 \times 10^6$ in specimen diluent with additives and $6.25 \times 10^6$ against spB4-2. This mouse was then boosted intravenously (via the tail vein) with 30 µg of the immunizing protein and used for fusion 3 days later.

D. Establishment of the Hybridomas

Normal mouse splenocytes were prepared by aseptically removing the spleen from a non-immunized mouse and crushing it using the plunger of a syringe through a screen that fits into a 60×15 mm Petri dish containing a small amount of Dulbecco's Minimum Essential (DME) medium. The splenocyte solution was washed with DME medium, and the red blood cells were lysed by adding 1 ml of 0.83% NH$_4$Cl in 10mM Tris to the cell pellet for 1 minute. The cells were again washed and resuspended in 40 mls of DME medium containing 20% Fetal Bovine Serum (FBS).

On the day of the fusion, the immunized mouse was sacrificed, and the spleen was removed and processed as described herein for the preparation of normal splenocytes except that the splenocytes were resuspended in 10 mls DME medium and counted. Splenocytes were fused in a 1:1 ratio with the SP2/0 myeloma cell line using the described modification of conventional methods (Kohler and Milstein, supra). Cells were plated at $1\times10^6$ splenocytes per well of a 24 multi-well tissue culture tray in 1.5 ml DME medium containing 20% FBS, hypoxanthine, aminopterin, and thymidine (HAT). After 24 hours, 200,000 normal splenocytes were added per 24 multi well (0.5 ml). HAT medium was added on day 5 and replaced on day 7.

Four of ninety initial hybrids from the fusion were positive for antibodies to HEV. Hybrid #67 (H67) had an optical density (O.D). of 0.988 when tested at a 1:100 dilution against 8-5 antigen-coated beads, was negative against CKS-only coated beads, and had an O.D. of 1.498 at a 1:100 dilution against HEV synthetic antigen spB4-2 beads. H67 was then cloned at one cell per well by limiting dilution technique as described in Goding, *Monoclonal Antibodies: Principles and Practices*, 2nd ed, Academic Press, New York [1986].

E. Establishment Of Clones By Limiting Dilution

The viable cells in the antibody positive wells were counted, and for each 96 multiwell tissue culture tray, an aliquot containing 100 cells was added to 20 mls of DME media containing 20% Fetal Bovine Serum (FBS) and $5\times10^6$ normal mouse splenocytes. An eight channel piperman adjusted to 0.2 ml was used to plant the cell suspension. The trays were incubated at 37° C. in a humidified 5% $CO_2$ incubator and refed on days 5 and 7 or as needed because of evaporation. When the wells containing growth were 30–50% confluent (usually between 10–21 days), those wells containing only 1 colony were sampled and tested for antibody activity. Several positive wells from each hybrid were selected and the cells were expanded. A single clone designated H67C46 resulted which had reactivity against HEV orf-3(8-5), and in particular, to the spB4-2 carboxy terminal region.

EXAMPLE 2

Production and Purification of the H67C46 Monoclonal Antibody

Clones selected for further evaluation were scaled up in tissue culture T-flasks and $10^6$ cells were injected into the peritoneal cavity of pre-pristaned BALB/c mice (Charles River Biotechnical Services, Inc., Wilmington, Mass.) (see Hurrell, supra). The resulting ascites fluid was harvested 7–10 days after injection, centrifuged and frozen. The antibody was affinity purified on a Protein A Sepharose CL-4B (Pharmacia-LKB Biotechnologies, Piscataway, N.J.). Bound monoclonal antibody was eluted from the column at a pH of 5.5, indicating its subtype as $IgG_1$.

EXAMPLE 3

Screening and Characterization of H67C46 Monoclonal Antibody

To screen and characterize the antibody, enzyme immunoassays (EIA's) were utilized which contained different antigens on the solid phase (polystyrene beads): the CKS-HEV recombinant orf-3 (8-5) (prepared as described in Example 1) was coated on the solid phase in either the unpurified (extracted and solubilized) form (ca. 50–60% pure HEV protein) or a purified protein (>90% pure), another EIA used the synthetic peptide spB4-2 on the solid phase, and to detect non-specific binding the solid phase was coated with CKS alone or a non-HEV CKS recombinant protein.

For all assays, mouse serum, tissue culture supernatant, mouse ascites fluid samples or monoclonal antibody (MAb) H67C46 obtained above were serially diluted 5 to 10-fold in specimen diluent containing phosphate-buffered-saline/Tris/EDTA, pH 7.8 with 20% goat serum, 10% fetal calf serum, 1% bovine serum albumin, 0.2% Triton-X 100, 0.1% sodium azide, with or without 1% *E. coli* lysate and 0.01% CKS added, then 200 µl was incubated with each solid phase for 1–2 hours at 40° C. Beads were then washed 3 times with 5 ml distilled water. Bound antibody was detected using 200 µl HRPO-labeled second antibody (Goat anti-mouse IgG H+L) from Kirkegaard and Perry Labs) at 0.3 µg/mL in conjugate diluent containing Tris-buffered-saline with 10% goat serum, 10% fetal calf serum and 0.15% Triton-X 100. Beads were incubated with conjugate for 1 hour at 40° C., and washed as before. O-Phenylenediamine (OPD) substrate was freshly prepared by adding 1 OPD tablet (Abbott) per 5 mls of OPD Diluent (Abbott), and 300 µl of OPD substrate solution was then added to each washed bead and incubated in the dark at room temperature for 30 minutes. One ml of sulfuric acid added to stop the reaction, and the amount of color generated was determined by measuring the absorbance of the substrate at 492 nm within 2 hours of sulfuric acid addition. Results given in Table 1 below indicate that the antibody was specific for the orf-3 region of HEV.

TABLE I

Characterization of H67C46 Monoclonal Antibody

| Dilution (−1) Clone H67C46 | Absorbance at 492 nm Recombinant HEV 8-5-coated bead | Recombinant CKS coated bead | HEV synthetic peptide spB4-2 |
|---|---|---|---|
| 10 | >2 | 0.042 | >2 |
| 1 × 10³ | >2 | 0.018 | >2 |
| 10 × 10³ | >2 | 0.012 | >2 |
| 100 × 10³ | >2 | 0.016 | >2 |
| 1 × 10⁶ | 0.636 | 0.013 | 0.685 |

EXAMPLE 4

Competitive Assay for Antibody to HEV:

Solid phase was coated with HEV orf-3 (8-5) or a combination of proteins coding for the orf-3 and orf-2 regions. The solid phases were pre-incubated with a 1:2 dilution of HEV negative human plasma (negative control) or human plasma known to contain HEV Ab (sample) in specimen diluent overnight at room temperature. Beads were then washed and monoclonal antibody (MAb) of the invention against HEV orf-3, diluted to give an O.D. of 1.000–1.500 when no inhibitor is present, was added to the appropriate beads and incubated for 1 hour at 40° C. The beads were then washed and HRPO-goat anti-mouse IgG (H+L) was added and incubated for 2 hours at 40° C. The beads were washed and label detection was performed using OPD substrate as described above.

Theoretically, a positive HEV Ab containing sample should reduce the signal 50%. In the example provided the HEV Ab positive sample showed 57.6% inhibition of MAb H67C46 when the 8-5 bead was used, and 35.3% inhibition when the HEV orf-2/orf-3 Combo bead was used. The results are given in Table II below.

TABLE II

Competitive Assay for Antibody to HEV orf-3

| | HEV BEAD | |
|---|---|---|
| | Recombinant Antigen for orf-3 % Inhibition | Recombinant Antigens for orf-2 and orf-3 % Inhibition |
| Pre-incubation with: | | |
| Specimen Diluent Only | — | — |
| Negative Human Plasma | — | — |
| Human anti-HEV + Plasma | 57.6 | 35.3 |

EXAMPLE 5

Competitive Assay for orf-3 Antigen to HEV

Solid phase is coated with HEV orf-3 (8-5) protein or with spB4-2 synthetic peptide. Monoclonal antibody (MAb) H67C46, at a concentration previously determined to give an O.D. of 1.000–2.000 in this assay format, is pre-incubated with sample at a time and temperature long enough to allow binding of HEV antigen in the sample to MAb (30–120 minutes, at room temperature to 40° C.). The solid phase is then added, and the mixture and bead are incubated at a time and temperature long enough to allow any remaining unbound MAb to bind to the solid phase (temperature range: room temperature to 40° C., time range: 1–16 hours). Binding of MAb to the solid phase is then detected either using a labeled second antibody (e.g. horseradish peroxidase (HRPO)-labelled Goat anti-mouse IgG) with incubation of 1–2 hours at 40° C., or MAb itself could be labeled, thus making the assay potentially performable in one step. Label detection is then performed (i.e. if using HRPO labeled Ab, add OPD substrate, incubate 30 minutes, add sulfuric acid to stop the reaction, and read at 492 nm). A positive, HEV antigen containing sample will inhibit with MAb for binding to the solid phase and reduce the signal at least 50%. Hybridoma cell line H67C46 was deposited with the American Type Culture Collection (A.T.C.C.), 12301 Parklawn Drive, Rockville, Md. 20852, on Jan. 12, 1994, and accorded A.T.C.C. Deposit Accession Number HB 11522.

What is claimed is:

1. A monoclonal antibody or fragment thereof which specifically binds to hepatitis E virus (HEV) orf-3-encoded protein, wherein said monoclonal antibody is secreted by a cell line ATCC deposit number HB 11522.

2. A hybridoma cell line which secretes a monoclonal antibody which specifically binds to hepatitis E virus (HEV) orf-3-encoded protein, wherein said cell line is ATCC deposit number HB 11522.

3. A competitive assay method for determining the presence of Hepatitis E Virus (HEV) antibody which may be present in a test sample, comprising:

a. contacting a test sample suspected of containing HEV antibodies with a solid phase coated with at least one HEV orf-3 antigen and an indicator reagent comprising a signal generating compound which generates a measurable signal and a monoclonal antibody which specifically binds to said HEV orf-3 antigen, for a time and under conditions sufficient to form antigen/antibody complexes of the test sample and solid phase and/or indicator reagent and solid phase; and b. determining the presence of HEV antibody present in the test sample by detecting the reduction in binding of the indicator reagent to the solid phase as compared to the signal generated from a negative test sample to indicate the presence of HEV antibody in the test sample, wherein said monoclonal antibody which specifically binds to said HEV orf-3 antigen is secreted by the cell line ATCC deposit number HB 11522.

4. The method of claim 3 wherein the signal generating compound is selected from the group consisting of a luminescent compound, a chemiluminescent compound, an enzyme and a radioactive element.

5. The method of claim 4 wherein said enzyme is selected from the group consisting of horseradish peroxidase, alkaline phosphatase and beta-galactosidase.

6. An assay kit for determining the presence of HEV antigen or antibody in a test sample comprising a container containing at least one monoclonal antibody or fragment thereof which specifically binds to HEV orf-3 antigen, wherein said monoclonal antibody is secreted by cell line ATCC deposit number HB 11522.

7. An immunoassay for detecting hepatitis E virus (HEV) antigen which may be present in a test sample comprising (a) contacting said test sample suspected of containing HEV antigen with a solid phase to which an HEV specific antibody is attached to form an antigen-antibody complex, (b) contacting said complex with an indicator reagent comprising an antibody attached to a label capable of generating a detectable signal wherein said indicator reagent specifically binds to said HEV antigen and (c) detecting the presence of HEV antigen in said test sample by detecting the signal generated by said indicator reagent, wherein the improvement comprises utilizing in either the solid phase of step (a) or the indicator reagent of step (b) a monoclonal antibody or fragment thereof, said monoclonal antibody secreted by the cell line ATCC deposit number HB 11522, wherein said monoclonal antibody or fragment thereof specifically binds to HEV orf-3 antigen.

* * * * *